United States Patent
Elkatatny et al.

(10) Patent No.: US 11,630,045 B2
(45) Date of Patent: Apr. 18, 2023

(54) AUTOMATED MARCH FUNNEL FOR OIL AND GAS FIELD OPERATIONS

(71) Applicant: KING FAHD UNIVERSITY OF PETROLEUM AND MINERALS, Dhahran (SA)

(72) Inventors: Salaheldin Elkatatny, Dhahran (SA); Rakan Fadhel, Dhahran (SA); Yazan Mheibesh, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

(21) Appl. No.: 16/384,241

(22) Filed: Apr. 15, 2019

(65) Prior Publication Data
US 2019/0323935 A1    Oct. 24, 2019

Related U.S. Application Data

(60) Provisional application No. 62/659,485, filed on Apr. 18, 2018.

(51) Int. Cl.
| | |
|---|---|
| *G01N 11/06* | (2006.01) |
| *E21B 21/01* | (2006.01) |
| *G01N 33/24* | (2006.01) |
| *G01G 17/06* | (2006.01) |
| *G01N 1/38* | (2006.01) |
| *E21B 41/00* | (2006.01) |

(52) U.S. Cl.
CPC ............. *G01N 11/06* (2013.01); *E21B 21/01* (2013.01); *E21B 41/00* (2013.01); *G01G 17/06* (2013.01); *G01N 1/38* (2013.01); *G01N 33/24* (2013.01)

(58) Field of Classification Search
CPC ...................................................... G01N 11/06
See application file for complete search history.

(56) References Cited

U.S. PATENT DOCUMENTS

| | | | | |
|---|---|---|---|---|
| 6,474,143 B1 * | 11/2002 | Herod | ...................... | G01N 9/32 73/32 R |
| 2007/0227234 A1 * | 10/2007 | Weisinger | .............. | G01N 11/06 73/54.13 |

(Continued)

FOREIGN PATENT DOCUMENTS

| | | |
|---|---|---|
| CN | 205607803 U | 9/2016 |
| CN | 207689315 U | 8/2018 |

OTHER PUBLICATIONS

Lee Toop, "In-line viscosity measurement, of drilling mud", https://www.oilandgasproductnews.com/articie/4180/in-line-viscosity-measurement-of-drilling-mud, Mar. 17, 2014, 4 pages.

(Continued)

*Primary Examiner* — Paul M. West
*Assistant Examiner* — Mark A Shabman
(74) *Attorney, Agent, or Firm* — Oblon, McClelland, Maier & Neustadt, L.L.P.

(57) ABSTRACT

The invention is directed to an automated Marsh funnel and Marsh funnel apparatus or system, and an automated method for measuring the Marsh funnel time and density of drilling muds and calculating other rheological properties from Marsh funnel time and mud weight. The system measures and reports rheological properties of drilling muds in real time and faster, more conveniently, and more accurately than conventional manual methods.

10 Claims, 8 Drawing Sheets

(56) References Cited

U.S. PATENT DOCUMENTS

| | | |
|---|---|---|
| 2011/0185795 A1 | 8/2011 | Colquhoun |
| 2012/0203463 A1* | 8/2012 | Guo .................. G01N 11/06 |
| | | 702/12 |
| 2014/0262516 A1* | 9/2014 | Larson .............. G01N 33/2823 |
| | | 175/48 |

OTHER PUBLICATIONS

Brian OCHOA, et al., "A New Sensor for Viscosity and Fluid Density Measurement for Oil Well Drilling Applications", Sensors and Measuring Systems, Jul. 4, 2014, pp. 1-6.

Salaheidin Elkatatny, et al., "Real time prediction of drilling fluid rheological properties using Artificial Neural Networks visible mathematical model (white box)", Journal of Petroleum Science and Engineering, vol. 146, 2016, pp. 1202-1210.

Salaheidin Elkatatny, "Real-Time Prediction of Rheological Parameters of KCI Water-Based Drilling Fluid Using Artificial Neural Networks", Arab J Sci Eng, vol. 42, 2017, pp. 1655-1665.

Khaled Abdelgawad, et al., "Real Time Determination of Rheological Properties of Spud Drilling Fluids Using a Hybrid Artificial Intelligence Technique", Journal of Energy Resources Technology, vol. 141, Mar. 2019, 9 pages.

Gulf Cooperation Council Office Action dated Sep. 30, 2020 in Gulf Cooperation Council Patent Application No. 2019-37390 (with English translation), citing document AA therein, 6 pages.

* cited by examiner

AUTOMATED MARCH FUNNEL FOR OIL AND GAS FIELD OPERATIONS

CROSS REFERENCE TO RELATED APPLICATION

This application claims priority to U.S. Provisional 62/659,485, filed Apr. 18, 2018, which is hereby incorporated by reference for all purposes.

BACKGROUND OF THE INVENTION

Field of the Invention

The invention falls within the fields of oil and gas drilling and involves equipment for automatically measuring the viscosity and other rheological properties of drilling mud or drilling fluid.

Description of Related Art

Determination of the rheological properties of drilling fluid is very important during drilling operations. Rheological properties affect many factors such as hole cleaning, rig hydraulic calculations, surge and swab pressure calculation, and selection of bit nozzles. Rheological properties such as plastic viscosity (PV), yield point (YP), and gel strength are measured using a rheometer usually twice a day. Other properties such as mud density and Marsh funnel are measured more frequently every 15 to 20 minutes to follow changes in mud properties.

A Marsh funnel has specific dimensions that are used to measure the time required to flow a certain volume of drilling fluid or drilling mud through the funnel as an indicator of the rheological properties of the drilling fluid. A Marsh funnel is a Marsh cone with a particular orifice and a working volume of 1,500 $cm^3$ as illustrated by FIG. 1; Marsh, H., *Properties and Treatment of Rotary Mud*, Transactions of the AIME 92 (1): 234-251 (1931). The funnel consists of a cone of 12 in long, and 6 in diameter at the top; and 2 in long tube at the bottom with 3/16 in internal diameter. A 1/8 in mesh screen is fixed near the top across half the cone to block large solid particles in the drilling fluid or drilling mud. Hossain, M. E. and Al-Majed, A. A. 2015. *Fundamentals of Sustainable Drilling Engineering*. Scrivener Publishing LLC. Using a Marsh funnel, a time in seconds for flowing 950 $cm^3$ of a drilling fluid or drilling mud through the March funnel is measured and recorded to determine viscosity and other parameters of the drilling fluid or drilling mud; Balhoff, M. T., Lake, L. W., Bommer, P. M., Lewis, R. E., Weber, M. J., and Calderin, J. M., 2011. *Rheological and yield stress measurements of non-Newtonian fluids using a Marsh Funnel*. Journal of Petroleum Science and Engineering 77 (3-4): 393-402. In normal operation, the funnel will be manually filled with the drilling fluid through the screen at the top and the orifice will be closed by the operator's finger. A stop watch is usually used to record the time required to flow 950 $cm^3$ of drilling mud through the Marsh funnel.

This process determines a Marsh funnel viscosity for the sample. A more viscous sample takes longer to flow through the March funnel than a sample with a lower viscosity. Correlations have been developed to convert the Marsh funnel viscosity to effective viscosity of drilling fluids as a function of drainage time and mud weight; Pitt, M. J. 2000. *The Marsh Funnel and Drilling Fluid Viscosity: A New Equation for Field Use. SPE Drilling and Completion* 15 (1): 3-6.

The viscosity of the drilling fluid is a very important parameter in drilling operation. The viscosity affects many parameters such as required pump pressure, friction loss calculation, and hole cleaning. In the field, drilling fluid viscosity is measured usually two times a day, while Marsh funnel viscosity and density are measured frequently every 10-15 minutes to give an indication of the changes in drilling fluid properties. However, more frequent, repeated and more accurate results are needed especially as drilling procedures become more automated and less reliant inaccurate manual measurements that vary when taken by different oilfield workers.

In view of the limitations of existing devices the inventors sought to design an automated and more accurate Marsh funnel system. The inventors sought to develop an automated system, apparatus and method less prone to human error and based on existing Marsh funnel devices. Another objective was to develop a system that can take accurate readings more frequently than manual readings taken every 15-20 minutes and a system that automatically calculates mud density and other rheological values.

As disclosed herein the inventors have developed a new device that is usable in the laboratory as well as in the field and which avoids inaccuracies attributable to human error as well as sampling problems, for example, those caused by sagging, where a top portion of drilling mud in holding tank loses viscosity due to settling of solid components into a lower portion of the drilling mud making the lower portion more dense.

BRIEF SUMMARY OF THE INVENTION

The invention provides an automated method, apparatus and system that more accurately and conveniently determines Marsh funnel time and drilling mud density than conventional manual methods that require two persons to perform the test and record the data. These conventional tests are usually done every 15 to 20 mins and the resulting data used to monitor changes in drilling fluid properties. However, manual procedures are subject to human error due to differences in how different people perform the test as well as physiological factors including how fatigued, busy or distracted a person taking the manual measurement is. Unlike conventional Marsh funnels which require two persons to perform the test and record the data and are subject to human error, the automated apparatus, system and method of the invention provide a repeatable and standardized way to determine Marsh funnel time, mud weight and density and other rheological properties of the drilling mud. Moreover, this method can be used to determine rheological properties such as rig hydraulic calculations every 2-10 minutes in real time with higher accuracy than manual measurements, for example, it takes repeated measurements with less variance, standard deviation, or statistical error than measurements manually taken by oil field personnel. The automated method of the invention, which also provides an optional automated way to clean the Marsh funnel between measurement intervals, frees drilling and rig personnel to conduct more important activities without interrupting Marsh funnel time readings. Furthermore, the automated method of the invention provides measurements of extended rheological properties, such as mud density, apparent viscosity, plastic viscosity, yield point, flow behavior index (n) and fluid consistency index K in real time that are not practical to calculate manually.

In addition to the higher accuracy, real time display of extended rheological properties of a drilling mud, the invention also provides a way to solve a problem of sagging such as barite sagging as shown by FIG. 2B, or the settling of solid materials in a drilling mud that produces less dense mud at the top of a drilling mud tank than the mud at the bottom of the tank. The automated system of the invention can take drilling mud samples from the bottom, middle and top of the tank to provide more accurate description of the homogeneity of the drilling mud in the tank.

The foregoing paragraphs have been provided by way of general introduction, and are not intended to limit the scope of the following claims.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 1:
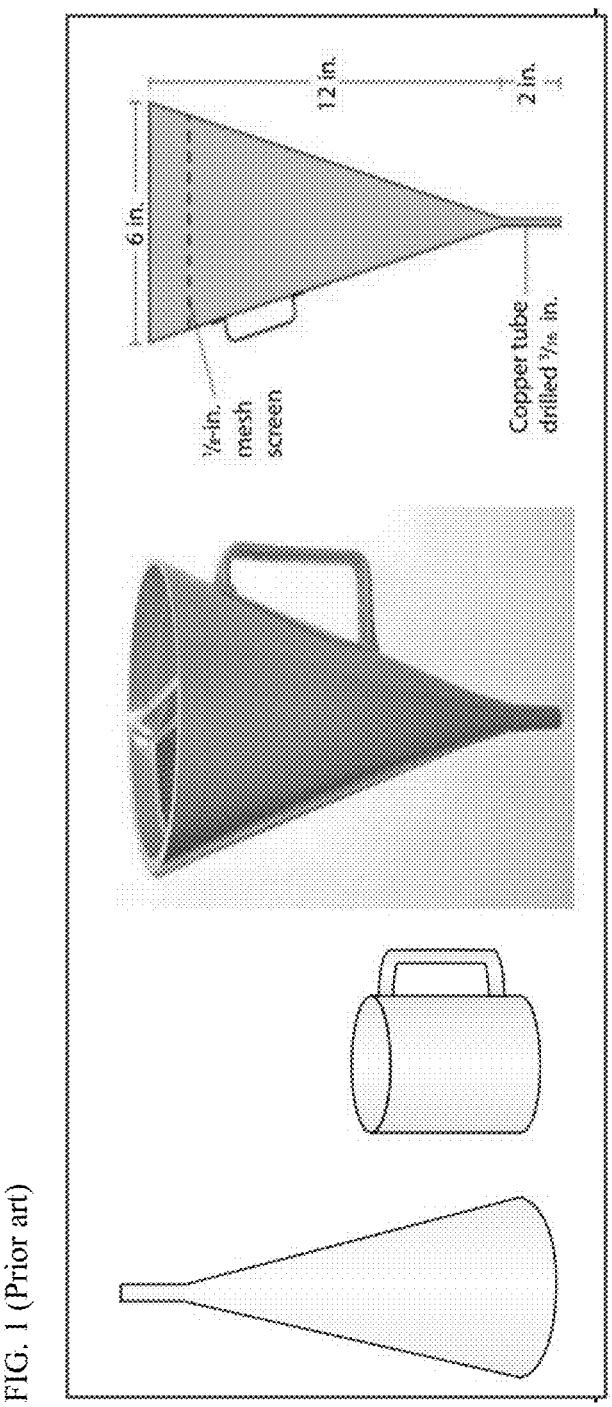
FIG. 1 shows a diagram of a Marsh funnel.
Figure 2A:
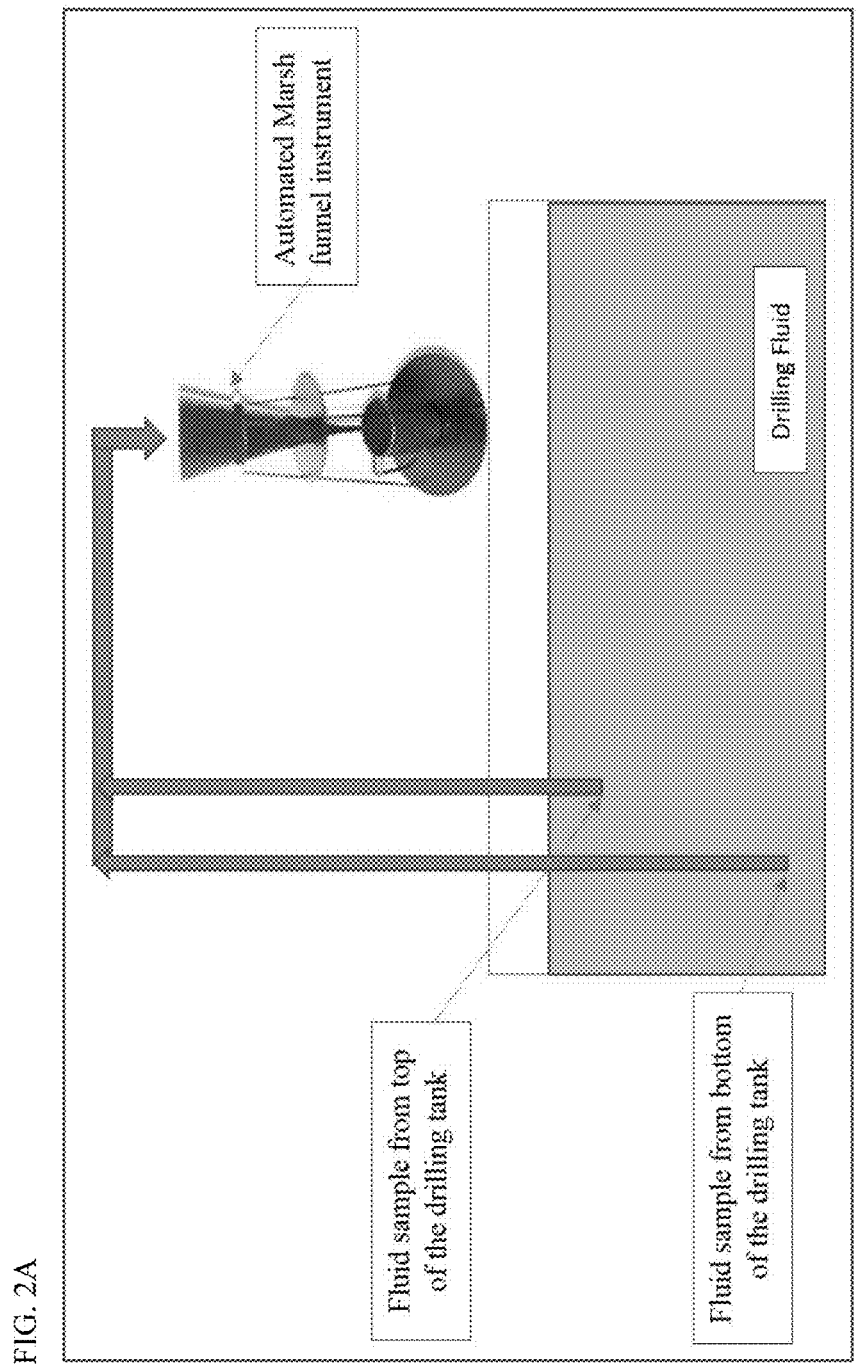
FIG. 2A shows an automated Marsh funnel instrument used for field applications.
Figure 2B:
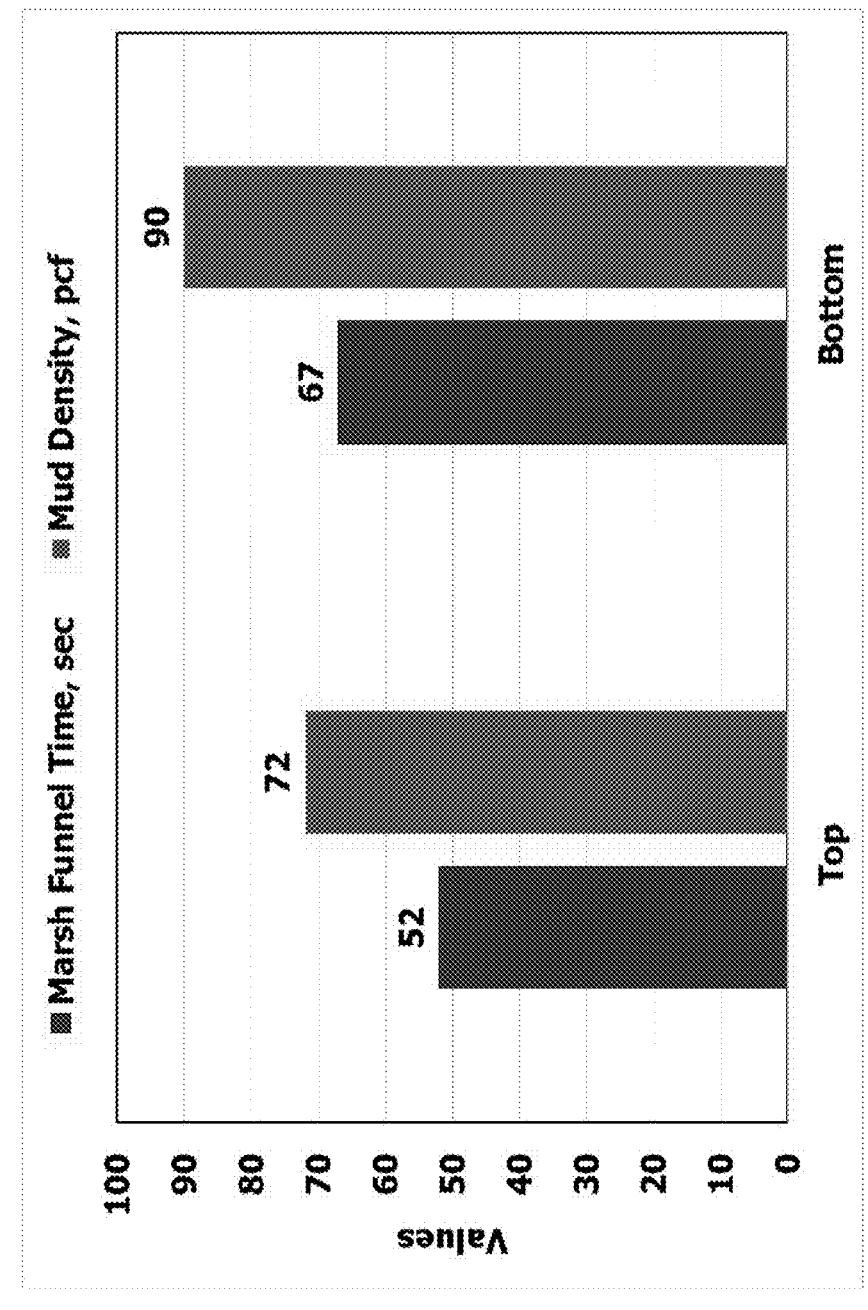
FIG. 2B shows a Marsh funnel and the drilling fluid density of barite water-based drilling fluid from a different position in the tank.
Figure 3:
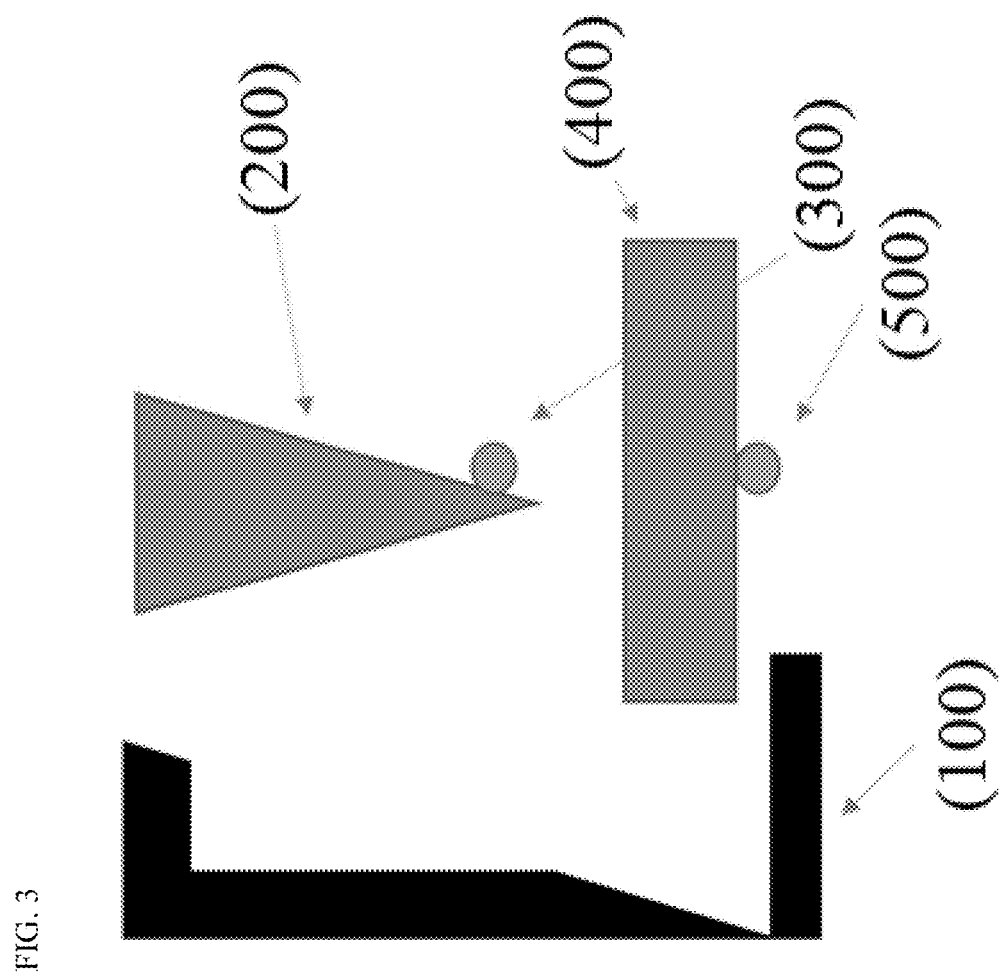
FIG. 3 shows different parts of the automated Marsh funnel system. Reference characters: (100) A Marsh funnel holder to keep the Marsh funnel in a vertical position. (200): Marsh funnel connected to a holder from the top and positioned to hold a time sensor (300) at the bottom. (400): fluid container connected to a mass balance for determining mud weight. (400): time sensor to start and stop flow at the bottom of the Marsh funnel. (500): Mass balance sensor.

Method of using Marsh Funnel system. When in operation, drilling mud flows from a mud tank or holding tank through one or more conduits into the top of a Marsh funnel having a closed valve at its lower end. A sensor at the end of the conduit or a fluid level sensor in the Marsh funnel stops the drilling mud flow when a predetermined volume of drilling mud (e.g. 1,500 cm$^3$) is deposited in the Marsh funnel.

An automated valve at the lower end of the Marsh funnel is opened by an electronic controller allowing a second predetermined volume (e.g., 950 cm$^3$) drilling mud sample to flow out of the Marsh funnel. A time sensor or fluid level sensor in the Marsh funnel or in a container above the scale or mass sensor detects and transmits or records the time between the opening of the valve and the passage of the second predetermined volume of mud sample through the March funnel when the valve closes. This sets a Marsh funnel time; e.g. the time for 950 cm$^3$ of a 1,500 cm$^3$ sample in a standard Marsh funnel to flow out the bottom of the funnel.

The automated Marsh funnel system includes an electronic controller that controls the gate or the one-way valve that allow only 950 cm$^3$ of the fluid to follow and automatically closed the valve record the time. In some embodiments a fluid level sensor in the mud container is used to stop the flow of mud by detecting and sending a signal to the controller to close the valve at the bottom of the Marsh funnel after discharge of the predetermined volume of mud (e.g., 950 cm$^3$ for a standard Marsh funnel).

The second predetermined volume of mud sample exiting the lower end of the Marsh funnel is weighed after being deposited in a mud container on a scale or mass sensor positioned under the Marsh funnel so as to determine the entire weight of the mud sample.

A mass sensor is used to measure the mud mass in the mud container. The measured parameters are flowing time and mud mass. Mud density is determined by dividing the weight of the sample by the predetermined volume of the sample.

So that multiple readings from subsequent drilling mud samples can be accurately made, the apparatus may incorporate an automated cleaning system to dispose of the mud sample and clean the Marsh funnel and the fluid container over the mass sensor so that they may receive another sample. These components may include a line, conduit or hose through which a liquid and/or gas cleaning material may pass through valve, nozzle or other aperture, which is opened by the electronic controller, and help flush out residual drilling mud and debris. In some embodiments a vacuum line may be used to remove residual material instead of, or in addition to cleaning with a liquid or gaseous cleaning material, such as water or an aqueous surfactant, a surfactant solution, or compressed air. One preferred method for cleaning the Marsh funnel system components comprises injecting water between readings in a direction away from the drilling tank. In a manner similar to that used for collecting a mud sample, water may be automatically injected and then removed from the system via a separate vacuum or suction line.

The apparatus of the invention may also include built-in code, chip or processor that uses the mud flow time and mass to find or predict: mud density, apparent viscosity, plastic viscosity, yield point, flow behavior index (n) and fluid consistency index K. All of the aforementioned properties are important in the drilling operation for rig hydraulics, hole cleaning efficiency, and drilling performance (e.g., determination of the rate of penetration).

The inventors developed different artificial intelligence codes or algorithms to determine the plastic viscosity, yield point, flow behavior index, flow consistency index, and apparent viscosity with high accuracy using the mass and funnel time for different drilling fluid types. For each drilling fluid type, there is AI code for each rheological property. In addition, the rheological properties are used to calculate the hole cleaning, rig hydraulic, equivalent circulation density, surge and swab pressure in real time which benefit from the frequent measurements of mass and Marsh funnel time by the system disclosed herein.

The results of these calculations are displayed on a monitor, such as digital monitor, can be output aurally in words, or can be output by other output devices.

The Marsh funnel apparatus can be connected to a computer which can categorize and save the data for later inspection or for further processing. Historical readings can be stored in computer memory. The processed data obtained from the Marsh funnel system is valuable as it permits estimates of pressure drops in the circulation system of a whole drilling rig and adjustment or optimization of drill cutting cleaning processes.

Embodiments of the invention include, but are not limited to the following.

An automated method for determining Marsh funnel time and drilling mud weight that includes automated transferring of a predetermined amount of a drilling mud from a tank, such as a holding tank, or other space, to a Marsh funnel at prearranged times or intervals, such as at intervals of 2, 3, 4, 5, 6, 7, 8, 9, 10, 12, 15, 20, 22, 25 to 30 minutes; automated releasing of the predetermined amount of drilling mud that has been transferred into the March funnel out the lower end of the Marsh funnel and measuring a time for it to pass out of the Marsh funnel ("Marsh funnel time"), and weighing the second predetermined amount of drilling mud exiting the Marsh funnel, thereby determining the Marsh funnel time and drilling mud weight of drilling mud; automatedly displaying, indicating, receiving or recording of the Marsh funnel time and weight of the sample, and automated cleaning and/or drying the Marsh funnel and weighing device prior to a subsequent automated transfer of a predetermined amount of a drilling mud into the Marsh funnel. Water may be pumped from a separate water tank and injected in the Marsh funnel cup and then removed to a disposal tank via a vacuum or suction line.

A sample of drilling mud may be pumped out of a holding tank via a conduit to a top of a Marsh funnel. At a prearranged time a valve, such as a mud valve, mud gate valve or other valve is opened for a time sufficient to flow a predetermined volume (e.g., 950 cm$^3$) of a sample of drilling mud into a Marsh funnel. The valve may be electronically opened and closed and may be part of an automated system for determining Marsh funnel time and mud weight and density. For example, the value may be open by a sensor that detects the presence of a first predetermined volume of mud (e.g. 1,500 cm$^3$) in the funnel and closed by a sensor that detects the presence of a second predetermined volume of mud (e.g. 950 cm$^3$) in the container attached to the scale or mass sensor. Other types of Marsh-like funnels having different dimensions, predetermined sample volumes or flow times may be used in some embodiments. Preferably, for the standpoint of obtaining up-to-date real time measurements of drilling mud rheological properties, samples are processed every 2, 3, 4, 5, 6, 7, 8, 9 or 10 mins and the apparatus cleared and cleaned at similar intervals so as to receive a subsequent mud sample.

This method may further include use of a computer, calculator or other data processor to determine from measured Marsh funnel time and mud density the other rheological properties of a drilling mud in real time such as plastic viscosity, yield point, flow behavior index, flow consistency index and/or an apparent viscosity of the drilling mud.

Drilling mud samples may be taken from a single location in a tank, such as a holding tank, such as from the top, bottom or middle of a tank or from a position adjacent or proximal to a tank mud intake line or a tank mud output line. In some embodiments, a sample will be taken from a mud tank having a mixing apparatus or agitator. In other embodiments, two or more samples may be taken from different locations in a holding tank, preferably in equal volumes and mixed prior to processing through the Marsh funnel. For example, a mixed sample with 50% of the volume taken from the bottom of a holding tank and 50% of the volume taken from the top of drilling mud in a holding tank may be used. In another embodiment, equal volumes of mud samples may be taken and mixed from three equidistant levels in the drilling mud in a holding tank.

In some embodiments, a thermometer or other temperature sensor is used to determine the temperature of mud samples, for examples, to detect temperature differences between samples taken from the bottom of a drilling mud holding tank and from the top of the drilling mud. In some embodiments, mud samples taken from different spaces in the holding tank may be brought to the same temperature, such as an ambient or room temperature, e.g. 15, 20, 25, 30, 35, 40, 45, 50, or 60° C., prior to being evaluated in the Marsh funnel. However, a temperature reading need not be taken, especially when temperatures at the bottom and top of the tank are similar.

In some embodiments, complete samples may be taken from different portions of the tank, for example, a first sample processed by the Marsh funnel may be from the top 10, 20, 30, 40, or 50% of the mud in a holding tank and a second sample taken from the bottom 10, 20, 30, 40 or 50% of the mud in a holding tank. This provides separate measurements of the rheological properties of mud in different portions of the tank and helps assess a degree of sagging in the holding tank mud. When individual, non-mixed mud samples are taken from different locations in a holding tank, they may be processed in any order, for example, samples from the top and bottom portions of drilling mud in a holding tank may be processed through the March funnel alternately.

In some embodiments, mud samples may be taken from spaces adjacent to drilling mud inputs into a holding tank or drilling mud outputs from a tank.

The method as disclosed herein may further include calculating from the Marsh funnel time and the drilling mud weight a plastic viscosity of the drilling mud. The method as disclosed herein may further include calculating from the Marsh funnel time and the drilling mud weight a yield point of the drilling mud. The method as disclosed herein may further include calculating from the Marsh funnel time and the drilling mud weight a flow behavior index of the drilling mud. The method as disclosed herein may further include calculating from the Marsh funnel time and the drilling mud weight a flow consistency of the drilling mud. The method as disclosed herein may further include calculating from the Marsh funnel time and the drilling mud weight an apparent viscosity of the drilling mud.

Another embodiment of the invention is a Marsh funnel apparatus. The apparatus may include a holder or housing configured to support or house a Marsh funnel in a substantially vertical position, an intake valve regulating the flow of a predetermined volume of drilling mud into the Marsh funnel at a predetermined interval or time, a Marsh funnel configured to hold a predetermined volume of mud, a valve at the bottom of the Marsh funnel configured to open and release the predetermined volume of mud from the Marsh funnel, a time sensor configured to measure an interval of time for the predetermined volume of mud to leave the Marsh funnel, a scale or balance configured to receive and weigh the predetermined volume of mud leaving the Marsh funnel. In some embodiments, the cost of producing such an apparatus is less than US $100-200.

In some embodiments, the Marsh funnel apparatus disclosed herein will include an apparatus for cleaning the Marsh funnel and scale prior to use with a subsequent drilling mud sample. Such an apparatus may include a hose, conduit and/or valve configured to remove debris by suction, or to release, spray or inject air or water or another cleaner into the Marsh funnel after the predetermined volume of drilling mud passes through the Marsh funnel, before the valve at the bottom of the Marsh funnel closes, and before a subsequent predetermined volume of mud is flowed into the Marsh funnel.

In some embodiments, the Marsh funnel disclosed herein will be a standard Marsh funnel and comprise a cone 6 inches across and 12 inches in height to the apex of which is fixed a tube 2 inches long and 3/16 inch internal diameter and in which a 10-mesh screen is fixed across half the cone in an upper half of the cone and wherein the predetermined volume of drilling mud is 950 cm$^3$.

The Marsh funnel apparatus may also include a container configured to receive and hold mud from the Marsh funnel while it is being weighed. The container may be configured so as to release the mud sample after weighing, for example, by tipping or inverting the container to displace the mud or by being equipped with an aperture which remains closed during weighing but opens after weighing so that the mud sample may ejected or washed out. The term "scale" as used herein unless otherwise indicated refers to any device useful for weight the mud sample, including a scale, balance, mass sensor or other weighing device. A scale may be reset to zero (tared) between the weighing of different samples to provide an accurate weight for a subsequent sample.

Another embodiment of the invention is an automated Marsh funnel system which includes a Marsh funnel apparatus as disclosed herein as well as other local or remote elements that provide or process a mud sample prior to flowing it into a Marsh funnel as well as control computer processor, or display or signaling elements which may be local or remote. This system includes at least one tank containing drilling mud, at least one conduit connecting the tank to at least one of the Marsh funnel apparatus as disclosed herein, a controller for the intake valve that sets a time between separate flows of the predetermined volume of mud into the Marsh funnel, and a device in communication with the time sensor and scale or balance that displays, indicates, receives, or records the time for the predetermined volume of mud to pass through the Marsh funnel and the weight of the predetermined sample or that transmits the time for the predetermined volume of mud to pass through the Marsh funnel and the weight of the predetermined sample to a computer.

This automated Marsh funnel system may include a drilling mud tank that has two or more outputs and wherein drilling mud samples from positions next to each output are separately taken and alternately flowed through the same Marsh funnel or flowed through different Marsh funnels, thereby providing separate Marsh funnel times and mud weights for each sample.

In the system disclosed may include a device in communication with the time sensor and scale or balance transmits the time for the predetermined volume of mud to pass through the Marsh funnel and the weight of the predetermined sample to a computer which calculates and displays or otherwise indicates the Marsh funnel time and drilling mud weight, a plastic viscosity, yield point, flow behavior index, flow consistency index and/or an apparent viscosity of the drilling mud.

The terms "drilling mud" or "drilling fluid" are used interchangeably herein unless otherwise specified. These terms encompass water-based muds (WBM), oil-based muds (OBM), invert emulsion, synthetic-based drilling fluid and other types of drilling fluids or drilling muds. A basic water-based mud (WBM) system begins with water, and then clays and other chemicals are incorporated into the water to create a homogenous blend. Oil-based muds can be a mud where the base fluid is a petroleum product such as diesel fuel. Synthetic-based muds (SBM) are muds where the base fluid is synthetic oil and are often used on offshore rigs because it has the properties of an oil-based mud, but the toxicity of the fluid fumes are much less than an oil-based fluid.

Drilling mud sample. The invention may be used to assess rheological properties of muds obtained from vertical, horizontal, deviated, multi-lateral wells and other well types. A predetermined volume of drilling mud is removed from a drilling fluid tank and placed into a Marsh funnel. This predetermined volume or sample of drilling mud may be taken from one or more positions in a drilling tank. For example, in a cylindrical or rectangular drilling tank it may be taken from a level at the bottom or top 5, 10, 15, 20, 25, 30, 35, 40, 45, 50, 55, 60, 65, 70, 75, 80, 85, 90, or 95% of the drilling fluid in the tank. In some embodiments, it is taken from a tank which mixes the drilling fluid and in others the sample may be taken from two or more positions within the tank, for example, from the top 10% of the drilling fluid and from the bottom 10% of the drilling fluid. Preferably, when the sample is taken from two or more positions in the tank, equal amounts of the drilling fluid are taken from each position and mixed. In other embodiments, the sample is taken from drilling fluid that has been premixed in the tank or where the sample is taken from a volume of drilling fluid exiting the drilling tank prior to or after further processing of the fluid and prior to pumping it into a borehole.

In other embodiments, a sample is taken from only one place in the tank. However, samples may be alternately taken from different positions in the tank so that rheological properties of the drilling mud at the top, one or more middle levels, or bottom of the drilling mud mass in a tank can be determined.

Drilling fluid tank. Mud tanks are divided into square tanks and cone-shaped tanks according to the shape difference of the tank bottom. The body of the tank is made by welding the steel plate and section, using a smooth cone-shape structure or the corrugated structure. The mud tank surface and passages can be made of slip resistant steel plate and galvanized steel plate. The surface of the tank can be equipped with a water pipeline for cleaning the surface and equipment on the tank, and can use soaked zinc processing for the galvanized steel plate.

The tanks are usually open-top and have walkways on top to allow a worker to traverse and inspect the level of fluids in the tanks. The walkways may also allow access to other equipment that is mounted on the top. Offshore drilling rigs usually have closed-in tanks for safety.

The mud tank is preferably sectioned off into different compartments. A compartment may include a settling tank, sometimes called a sand trap, to allow sand and other solids in the drilling fluid to precipitate before it flows into the next compartment. Other compartments may have agitators on the top, which have long impellers extending into the tank for stirring fluids to thereby prevent precipitating and/or settling. Mud guns are often equipped at the corners of the tanks' top, spraying high-pressure fluids (e.g., mud) to prevent the drilling fluids in the corner of the compartment from precipitating. The piping linking the mud tanks/pits with the mud pumps is called the suction line. This may be gravity fed or charged by centrifugal pumps to provide additional volumetric efficiency to the mud pumps.

Marsh funnel. This term as used herein refers to a conventional Marsh funnel design as well as to other cones with different geometries and orifice arrangements which are called flow cones, but have the same operating principle. Based on a method published in 1931 by H. N. Marsh, a Marsh cone is a flow cone with an aspect ratio of 2:1 and a working volume of at least one litre. A Marsh funnel is a Marsh cone with a particular orifice and a working volume of 1.5 liters. It consists of a cone 6 inches (152 mm) across and 12 inches in height (305 mm) to the apex of which is fixed a tube 2 inches (50.8 mm) long and 3/16 inch (4.76 mm) internal diameter. A 10-mesh screen is fixed near the top across half the cone. Typically the volume collected is a quart. If water is used, the time should be 26+/−0.5 seconds. If the time is less than this the tube is probably enlarged by erosion, if more it may be blocked or damaged, and the funnel should be replaced. In some companies, and Europe in particular, the volume collected is a liter, for which the water funnel time should be 28 seconds. Marsh disclosed collecting 0.50 liter, for which the time was 18.5 seconds.

The Marsh funnel time is often referred to as the Marsh funnel viscosity, and is represented by the abbreviation FV. The unit (seconds) is often omitted. Formally, the volume should also be stated. The (quart) Marsh funnel time for typical drilling muds is 34 to 50 seconds, though mud mixtures to cope with some geological conditions may have a time of 100 or more seconds. While the most common use is for drilling muds, which are non-Newtonian fluids, the Marsh funnel is not a rheometer, because it only provides one measurement under one flow condition. However, the effective viscosity can be determined from the following formula:

$\mu = \rho(t-25)$, where $\mu$=effective viscosity in centipoise, $\rho$=density in g/cm$^3$, t=quart funnel time in seconds. For example, a mud having a funnel time of 40 seconds and density 1.1 g/cm$^3$ has an effective viscosity of about 16.5 cP. For the range of times of typical muds above, the shear rate in the Marsh funnel is about 2000$^{-5}$. See Pitt, M. J. 2000. The Marsh Funnel and Drilling Fluid Viscosity: A New Equation for Field Use. *SPE Drilling and Completion* 15 (1): 3-6.

Mud weight. In the oil industry, mud weight is the density of the drilling fluid and is normally measured in pounds per gallon (lb/gal) (ppg) or pound cubic feet (pcf). In the field it is measured using a mud scale or mud balance. In conventional drilling fluids, barite is used to increase the density. Although other additives such as halite (salt) or calcium carbonate can also be used. Mud weight can be decreased by dilution or solids control equipment such as an industrial centrifuge, desilter, desander and shale shaker. Mud weight is used to control trapped fluids or gas in the formations by hydro static pressure, increasing the mud weight=increasing the hydrostatic pressure. If the hydrostatic pressure is increased over the formation's pressure a fracture will form in the formation leading to loss of the mud to the formation. This loss can be addressed by adding a loss circulation material like gel-flake or wood chips to the mud that acts to refill the gap and stop mud loss. If the mud loss continues, then the hydrostatic pressure will decrease and flammable fluids and gas trapped under pressure will start leaking to the surface.

Plastic viscosity. A measure of the internal resistance to fluid flow of a Bingham plastic, expressed as the tangential shear stress in excess of the yield stress divided by the resulting rate of shear.

Yield point. YP is the yield stress extrapolated to a shear rate of zero. (Plastic viscosity, PV, is another parameter of the Bingham-plastic model.) A Bingham plastic fluid plots as a straight line on a shear rate (x-axis) versus shear stress (y-axis) plot, in which YP is the zero-shear-rate intercept. (PV is the slope of the line.) YP is calculated from 300- and 600-rpm viscometer dial readings by subtracting PV from the 300-rpm dial reading. YP is used to evaluate the ability of a mud to lift cuttings out of the annulus. A high YP implies a non-Newtonian fluid, one that carries cuttings better than a fluid of similar density but lower YP. YP is lowered by adding deflocculant to a clay-based mud and increased by adding freshly dispersed clay or a flocculant, such as lime.

Flow behavior index. The flow behavior index (n) indicates the degree of non-Newtonian characteristics of the fluid. As the fluid becomes more viscous, the consistency factors (k) increases; as a fluid becomes more shear thinning "n" decreases. When "n" is 1 the fluid is Newtonian.

Flow consistency index (K). A power-law fluid, or the Ostwald-de Waele relationship, is a type of generalized Newtonian fluid (time independent Non-Newtonian fluid) for which the shear stress, $\tau$, is given by:

$$\tau = K\left(\frac{\partial u}{\partial y}\right)^n;$$

where: K is the flow consistency index (SI units Pa s$^n$), $\partial u/\partial y$ is the shear rate or the velocity gradient perpendicular to the plane of shear (SI unit s$^{-1}$), and n is the flow behavior index (dimensionless). The quantity:

$$\mu_{eff} = K\left(\frac{\partial u}{\partial y}\right)^{n-1}$$

represents an apparent or effective viscosity as a function of the shear rate (SI unit Pa s).

The value of K and n can be obtained from graph off $\log(\mu_{eff})$ and $$\log\left(\frac{\partial u}{\partial y}\right).$$

The slope line gives the value of n−1 from which n can be calculated. The intercept at $$\log\left(\frac{\partial u}{\partial y}\right) = 0$$

gives the value of K.

Apparent viscosity. Apparent viscosity (sometimes denoted η) is the shear stress applied to a fluid divided by the shear rate:

$$\eta = \frac{\tau}{\dot{\gamma}}.$$

For a Newtonian fluid, the apparent viscosity is constant, and equal to the Newtonian viscosity of the fluid, but for non-Newtonian fluids, the apparent viscosity depends on the shear rate. Apparent viscosity has the SI derived unit Pa·s (Pascal-second, but the centipoise is frequently used in practice: (1 mPa·s=1 cP).

Other methods for determining properties of drilling fluids based on Marsh funnel time and mud density include those of Almandawi, F. H., Al-Yaseri, A. Z, and Jasim, N. 2014. *Apparent Viscosity Direct from Marsh Funnel Test*. Iraqi Journal of Chemical and Petroleum Engineering 15 (1): pp. 51-57. They concluded that Eq. (2) related the apparent viscosity to Marsh funnel viscosity and it gives more accurate results than Eq. (3) and found out that the constant of 28 is more appropriate than 25, obtained by Pitt, id. (2000).

$$AV=D(T-25) \quad (1)$$

$$AV=-0.0118*T^2+1.6175*T-32.168 \quad (2)$$

$$AV=D(T-28) \quad (3)$$

Where AV is apparent viscosity which can be measured in cP; D is fluid density measurable in (g/cm$^3$) and T is Marsh funnel time measured in seconds.

Equations using regression techniques can also be used to obtain the rheological properties of the drilling fluid using Marsh funnel and mud density such as those described by, Equations (4)-(7) below may also be used; Elkatatny, S. M. 2017. *Real Time Prediction of Rheological Parameters of KCl Water-Based Drilling Fluid Using Artificial Neural Networks*. Arabian Journal of Science and Engineering 42(4): pp. 1655-1665.

$$PV=17.735*D*\log T-30.9-7.979 \quad (4)$$

$$YP=1.5492*D*\log T-30.9+18.84 \quad (5)$$

$$AV=18.833*D*\log T-30.9+0.9186 \quad (6)$$

$$\eta=0.1193*D*\log T-11.249+0.3459 \quad (7)$$

The inventors developed different regression and AI codes for every rheological parameter. For example, using equations 4 to 7 when the mud weight was 1.12 g/cm$^3$ and the Marsh funnel time was 65 sec, the plastic viscosity was 22.18 cP, the yield point was 22.33 lb/100 ft$^2$, the apparent viscosity was 33.3 cP, the flow behavior index (n) was 0.597, and the flow consistency index was 1.061 lb/100 ft$^2$.

Alternatively, Marsh funnel time, drilling fluid density, and the solid content can be used to determine the rheological properties of the drilling fluid using artificial neural network based on an equation to determine PV, YP, apparent viscosity (AV), flow consistency index and flow behavior index for invert emulsion and KCl polymer mud; Elkatatny, S. M., Zeeshan, T., and Mahmoud, M. A. 2016. *Real Time Prediction of Drilling Fluid Rheological Properties Using Artificial Neural Networks Visible Mathematical Model (White Box)*, Journal of Petroleum Science and Engineering. 146: pp. 1202-1210 and Elkatatny, S. M., Zidan, K. and Mahmoud, M. 2017. *Determination of the Rheological Parameters of Invert Emulsion Drilling Fluid in Real Time using Non-Linear Regression Technique*. Petroleum & Petrochemical Engineering Journal.

These above drilling fluid properties and parameters are often too complex to solve in real time. In view of this problem computer implemented calculations based on Marsh funnel time and mud density may be used.

Figure 4:
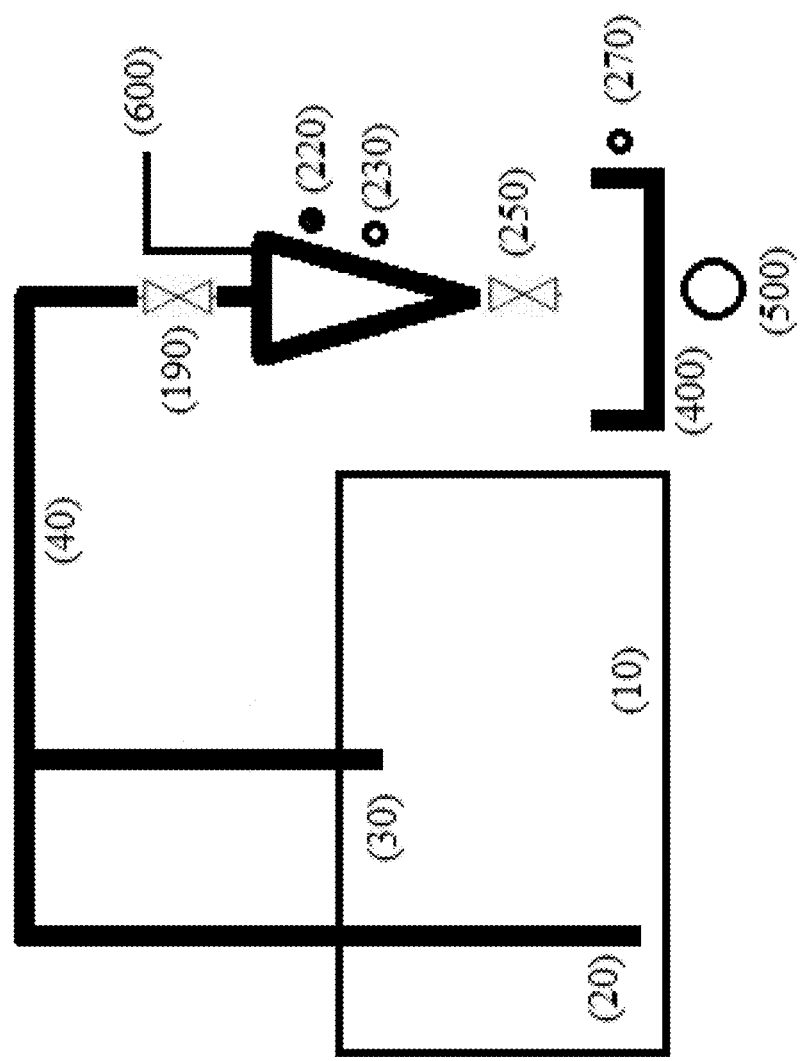
FIG. 4 depicts an embodiment of the automated Marsh funnel. Reference characters: (10) drilling mud holding tank, (20) and (30) upper and lower feeds, (40) conduit between tank and Marsh funnel, (190) input valve, (220) sensor for first predetermined volume of drilling fluid, (230) and/or (270) time sensors that detect when the second predetermined volume of drilling fluid has flowed through valve (250) into (400) container attached to (500) mass sensor. Line (600) dispenses cleaning fluids or gases and cleans the Marsh funnel prior to the taking of a new reading.

Valves. A valve is a device that regulates, directs or controls the flow of a fluid (gases, liquids, fluidized solids, emulsions, or slurries) by opening, closing, or partially obstructing various passageways. As used herein, this term includes fittings, gates or other apertures that can be opened and closed so as to permit the flow of a drilling mud sample. The Marsh system preferably uses a gate valve at the discharge end of the funnel (e.g., position 250 in FIG. 4). Valves that control flushing of the funnel through apertures are preferably located equidistant around the circumference of the top opening of the funnel, preferably there is at least one flushing aperture every 45 degrees each separately connected to a valve. Other valve or flushing aperture configurations that effectively clean the Marsh funnel system between readings may also be used, such as use of 1, 2, 3, 4, 5, 6 or more flushing apertures.

Controller. As used herein a controller is typically and electronic or mechanical element that sends a signal to a valve to open and close. The controller is typically linked to a sensor on an intake valve between a drilling fluid conduit and a valve positioned at the top of a Marsh funnel and to a valve positioned at the lower end of the Marsh funnel. At a predetermined time the controller transmits a signal to the intake valve to release a first predetermined volume (e.g., 1,500 cm$^3$) of drilling mud into the Marsh funnel and then for the valve to close. It then transmits a signal to the valve at the lower end of the Marsh funnel to open and release a second predetermined volume (e.g., 950 cm$^3$) from the Marsh funnel to the weighing device. The controller closes the lower valve upon release of the second predetermined volume of drilling mud and receives a signal from the weighing device when the weight of the sample has been determined. The controller then opens the lower valve and sends a signal to trigger the washing device to wash and/or dry the Marsh funnel and weight device, for example, by opening a washer valve and releasing of a stream of water and/or air through the Marsh funnel or over the weight device. It then sends a signal to the lower Marsh funnel valve and washer valve to close. The processor is typically in communication with one or more fluid level sensors to detect the first and/or second predetermined drilling mud volume respectively dispensed into, or out of, the Marsh funnel. The process is also typically in communication with a clock or timing device that sets a time between repeated measurements by the Marsh funnel device. Process controllers are known in the art and include the controllers or control systems described by Hypertext transfer protocol available at //en.wikipedia.org/wiki/Process_control (last accessed Mar. 24, 2019).

Data processor. The automated Marsh funnel of the invention preferably integrates a data processor that receives the Marsh funnel time and mud weight data from the automated Marsh funnel, and calculates mud density and other rheological values from these data. It may further adapt the calculated rheological values for display on a visual monitor or other system, such as a remote computer system monitor. In some embodiments, the process controller of the Marsh funnel and the data processor will be integrated or will both be incorporated into the automated Marsh funnel. In other embodiments, the data processor and/or display or data output may be remote, for example, the data from the automated Marsh funnel may be received by a computer in a control room remote from the drilling mud holding tank or automated Marsh funnel.

Cleaner. To provide more accurate results, the automated Marsh funnel of the invention is preferably equipped with a system for cleaning and/or drying the Marsh funnel and weight device between uses to remove any residual drilling mud or debris from a previous cycle. This may be done mechanically (e.g., by tipping the funnel or weighing device to spill off residual drilling mud) or by washing the funnel and weighing device with a fluid or gas, such as with water, a surfactant solution or with air. Liquids and gases may be dispensed via lines, apertures, valves or nozzles or other fittings that contact the washing fluid or gas with surfaces of the funnel or weight device containing residual drilling mud. A no contact water level sensor which allows 950 $cm^3$ of drilling fluid to be filled in the cup, an electrical valve that opens and closes the Marsh funnel orifice, a balance sensor which gives the weight of the mud in the cup, and an Ardino unit which controls the whole system may be used.

Figure 5:
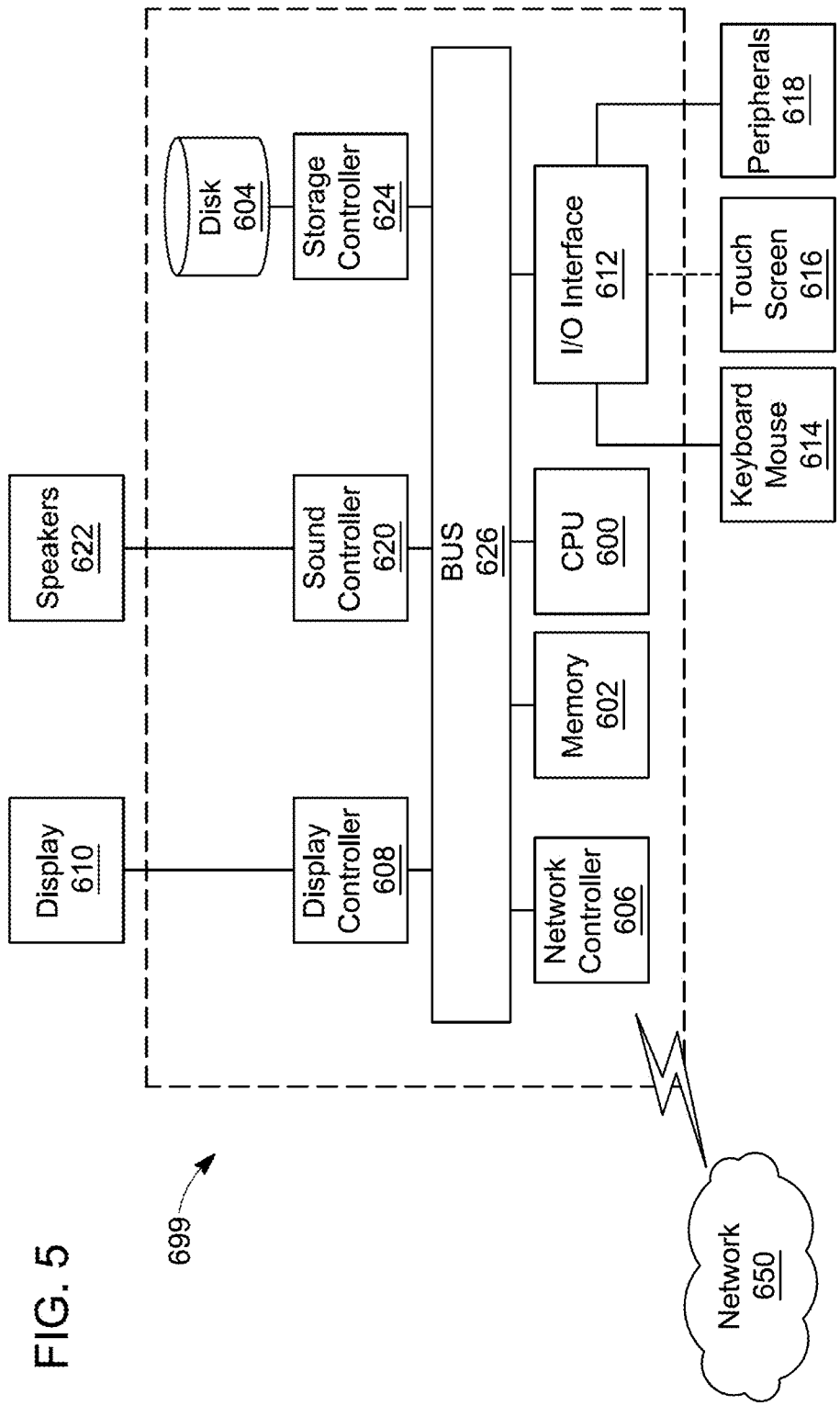
FIG. 5. illustrates a computer system upon which embodiments of the present disclosure may be implemented.
Figure 6:
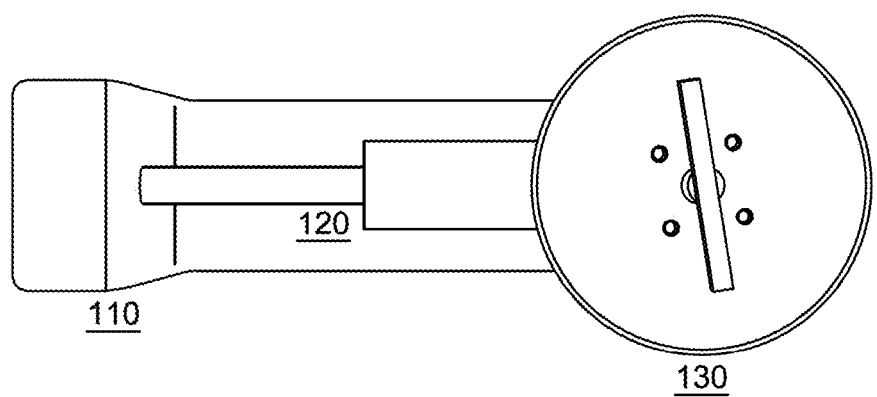
FIG. 6. Top view showing cleaning nozzles. (110) stand; (120) holder(s) and power supply; (130) top view of fitting containing entry for fluid samples and for cleaning nozzles.
Figure 7:
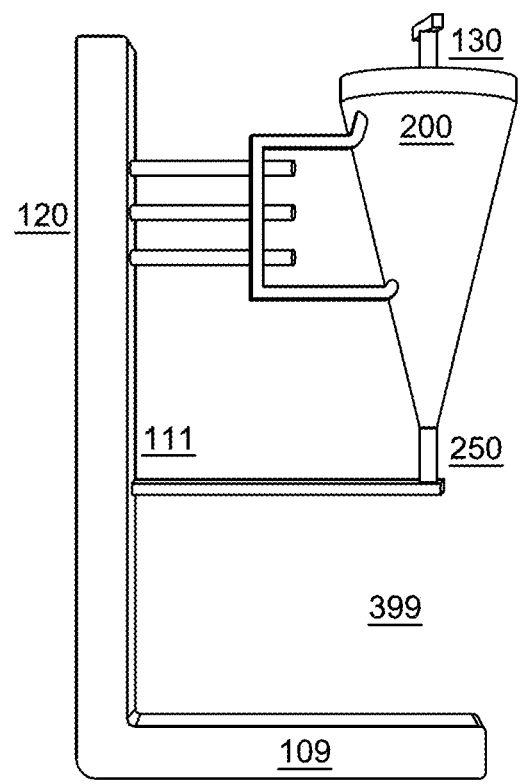
FIG. 7. 3D design of automated Marsh funnel (side view). (109): base with embedded sensor for mass measurements; (110) stand, (120) holders and power supply; (130) fitting containing entry for fluid samples and cleaning nozzles; (200) Marsh funnel; (250) automated valve; (399) space for Marsh funnel cup or container (400).

Computer implemented control of apparatus, measurement of viscosity properties and display or recording of viscosity properties of a drilling mud or fluid. In some embodiments, the invention may be implemented using a computer system as a processor, calculator, or display. FIG. 5 illustrates a computer system upon which embodiments of the present disclosure may be implemented. Each of the functions of the above described embodiments may be implemented by circuitry, which includes one or more processing circuits. A processing circuit includes a particularly programmed processor, for example, processor (CPU) 600, as shown in FIG. 5. A processing circuit also includes devices such as an application specific integrated circuit (ASIC) and conventional circuit components arranged to perform the recited functions.

In FIG. 5, the device 699 includes a CPU 600 which performs the processes described above including taking and moving a sample from a drilling fluid tank, dispensing it into a March funnel, releasing the sample from the Marsh funnel, detecting and reporting or recording the time for the sample to move through the Marsh funnel scanning, calculating and displaying a Marsh funnel time, weighing the sample, determining one or more properties of the sample and displaying or recording the results, including Marsh funnel time, sample, weight, sample density and other properties of the sample.

The device 699 may be a general-purpose computer or a particular, special-purpose machine. In one embodiment, the device 699 becomes a particular, special-purpose machine when the processor 600 is programmed to participate in processing viscosity data and/or performing one or more steps of the method described herein.

The process data and instructions may be stored in memory 602. These processes and instructions may also be stored on a storage medium disk 604 such as a hard drive (HDD) or portable storage medium or may be stored remotely. The instructions may be stored on CDs, DVDs, in FLASH memory, RAM, ROM, PROM, EPROM, EEPROM, hard disk or any other device with which the system communicates, such as a server or computer. In other words, the instructions may be stored on any non-transitory computer-readable storage medium to be executed on a computer.

Further, the discussed embodiments may be provided as a utility application, background daemon, or component of an operating system, or combination thereof, executing in conjunction with CPU 600 and an operating system such as, but not limited to, Microsoft Windows, UNIX, Solaris, LINUX, Android, Apple MAC-OS, Apple iOS and other systems known to those skilled in the art.

CPU 600 may be any type of processor that would be recognized by one of ordinary skill in the art. For example, CPU 600 may be a Xenon or Core processor from Intel of America or an Opteron processor from AMD of America. CPU 600 may be a processor having ARM architecture or any other type of architecture. CPU 600 may be any processor found in a mobile device (for example, cellular/smart phones, tablets, personal digital assistants (PDAs), or the like). CPU 600 may also be any processor found in musical instruments (for example, a musical keyboard or the like).

Additionally, or alternatively, the CPU 600 may be implemented on an FPGA, ASIC, PLD or using discrete logic circuits, as one of ordinary skill in the art would recognize. Further, CPU 600 may be implemented as multiple processors cooperatively working in parallel to perform the instructions of the processes described herein.

The computer 699 in FIG. 5 also includes a network controller 606, such as, but not limited to, a network interface card, for interfacing with network 650. As can be appreciated, the network 650 can be a public network, such as, but not limited to, the Internet, or a private network such as an LAN or WAN network, or any combination thereof and can also include PSTN or ISDN sub-networks. The network 650 can also be wired, such as an Ethernet network, or can be wireless such as a cellular network including EDGE, 3G, 4G or 5G wireless cellular systems. The wireless network can also be Wi-Fi, Bluetooth, or any other wireless form of communication that is known.

The computer 699 further includes a display controller 608, such as, but not limited to, a graphics adaptor for interfacing with display 610, such as, but not limited to, an LCD monitor. A general purpose I/O interface 612 interfaces with a keyboard and/or mouse 614 as well as a touch screen panel 616 on or separate from display 610. General purpose I/O interface also connects to a variety of peripherals 618 including printers and scanners. The peripheral elements discussed herein may be embodied by the peripherals 618 in the exemplary embodiments.

A sound controller 620 may also be provided in the computer 699 to interface with speakers/microphone 622 thereby providing sounds and/or music. The speakers/microphone 622 can also be used to accept dictated words as commands.

The general purpose storage controller 624 connects the storage medium disk 604 with communication bus 626, which may be an ISA, EISA, VESA, PCI, or similar. A description of the general features and functionality of the display 610, keyboard and/or mouse 614, as well as the display controller 608, storage controller 624, network controller 606, sound controller 620, and general purpose I/O interface 612 is omitted herein for brevity as these features are known As described above, the device and system of the invention provides an automated Marsh funnel that provides excellent and more accurate results in real time than those obtained by manual or human measurement of drilling fluid viscosity and other properties. Moreover, the automated Marsh funnel viscosity values can be used to determine different parameters such as; apparent viscosity, plastic viscosity, and yield point providing a more detailed description of the properties of drilling fluid or drilling mud in real time. The invention provides this information automatically and in real time. Moreover, it permits more frequent and accurate measurements of the properties of a drilling fluid in real time to operators of oil and gas drilling equipment.

EXAMPLE

Fluid from a drilling mud holding tank is flowed from the mud tank to the Marsh funnel. A sensor in the Marsh funnel stops the flow when 1500 cm$^3$ of mud have been flowed into the funnel. A valve at the bottom of the funnel is opened to start the flow of mud from the funnel into a mud container on a scale. A fluid level sensor in the mud container stops the flow of mud by closing the valve at the bottom of the Marsh funnel. During this operation, a time sensor is used to measure the time needed for the fluid flow from the funnel to fill the mud container until 950 cm$^3$ is reached or simply the time from opening the valve at the bottom of the funnel until closing it. A mass sensor is used to measure the mud mass in the mud container. From the measured parameters of flowing time and mud mass, a built-in processor or device programed to calculate other rheological properties from mud flow time (Marsh funnel time) and mud mass to find: mud density, apparent viscosity, plastic viscosity, yield point, flow behavior index (n) and fluid consistency index K as describe herein. The results obtained showing the rheological properties of the mud sample are shown on a digital screen and data obtained or derived from the mud flow and mud mass readings are stored or further processed. By processing these data, pressure drops in the circulation system of a whole drilling rig can be estimated and used to optimize the drill cutting cleaning process. An automated cleaning system is used to clean the Marsh funnel, and scale and fluid container and dispose the previous mud sample.

Terminology. Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by deletion of http: or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all subranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. An automated method for determining Marsh funnel time and drilling mud weight, comprising:
   transferring a first predetermined amount of a drilling mud via at least one conduit from a holding tank to a Marsh funnel every 2 to 30 minutes, wherein the first predetermined amount is dispensed via opening and closing of an intake valve between the at least one conduit and the Marsh funnel under the control of an electronic controller in communication with a fluid level sensor,
   wherein a first half of the first predetermined amount of drilling mud is taken from a 20 vol. % of drilling mud in an upper end of the holding tank and a second half is taken from a 20 vol. % of drilling mud in a lower end of the holding tank and mixed prior to dispensing via the intake valve between the at least one conduit and the Marsh funnel;
   releasing a second predetermined amount of drilling mud in the Marsh funnel from an automated valve at a lower end of the Marsh funnel under the control of the electronic controller in communication with a second fluid level sensor or time sensor that measures a time for the second predetermined amount of drilling mud to leave the Marsh funnel (Marsh funnel time);
   weighing the second predetermined amount of drilling mud on an automated weighing device in communication with the electronic controller,
   thereby determining a Marsh funnel time and a drilling mud weight of the second predetermined volume of drilling mud;
   transmitting the Marsh funnel time and the drilling mud weight to an electronic data processor;
   displaying, indicating, receiving or recording of the Marsh funnel time and weight of the second predetermined amount of drilling mud on a screen or other output device; and
   cleaning and/or drying the Marsh funnel and the automated weighing device prior to a subsequent automated transfer of a third predetermined amount of a drilling mud into the Marsh funnel by releasing a residual mud in the Marsh funnel by reopening the automated valve at the lower end of the Marsh funnel after the second predetermined amount of drilling mud has been weighed, opening at least one cleaning valve which dispenses a cleaning liquid and/or a gas through at least one aperture into the Marsh funnel and/or over the automated weighing device or which removes drilling mud by vacuum, and reclosing the automated valve at the bottom of the Marsh funnel after cleaning and/or drying,
   wherein the electronic controller opens and closes the intake valve between the conduit and Marsh funnel, the automated valve at the bottom of the Marsh funnel, and the at least one cleaning valve.

2. The automated method of claim 1, wherein automated transferring of the first predetermined amount of a drilling mud from the holding tank to the Marsh funnel is done every 5 to 10 minutes.

3. The automated method of claim 1, further comprising calculating on the electronic data processor in real time from the Marsh funnel time and drilling mud weight, a plastic viscosity, a yield point, a flow behavior index, a flow consistency index and/or an apparent viscosity of the drilling mud and displaying, indicating, receiving or recording of the plastic viscosity, the yield point, the flow behavior index, the flow consistency index and/or an apparent viscosity of the drilling mud on a screen or other output device.

4. The method of claim 1, wherein the first predetermined amount of a drilling mud is taken from a holding tank equipped with a drilling mud mixer or agitator.

5. The method of claim 1, wherein the first predetermined amount of the drilling mud is taken from a location next to a tank output for the drilling mud.

6. The method of claim 1, further comprising calculating, by the electronic data processor, a plastic viscosity of the drilling mud from the Marsh funnel time and the drilling mud weight.

7. The method of claim 1, further comprising calculating, by the electronic data processor, a yield point of the drilling mud from the Marsh funnel time and the drilling mud weight.

8. The method of claim 1, further comprising calculating, by the electronic data processor, a flow behavior index of the drilling mud from the Marsh funnel time and the drilling mud weight.

9. The method of claim 1, further comprising calculating, by the electronic data processor, a flow consistency of the drilling mud from the Marsh funnel time and the drilling mud weight.

10. The method of claim 1, further comprising calculating, by the electronic data processor, an apparent viscosity of the drilling mud from the Marsh funnel time and the drilling mud weight.

* * * * *